(12) United States Patent  
Liu

(10) Patent No.: US 7,789,855 B2  
(45) Date of Patent: Sep. 7, 2010

(54) BARREL TYPE PLUNGER FOR USE WITH A NEEDLE-RETRACTABLE SAFETY SYRINGE AND THE SYRINGE USING THE SAME

(76) Inventor: Wenjie Liu, Beijing Wan Te Fu Medical Apparatus Co., Ltd., Nian Tou Industry Zone, Ma chi kou Town, Changping District, Beijing (CN)

( * ) Notice: Subject to any disclaimer, the term of this patent is extended or adjusted under 35 U.S.C. 154(b) by 100 days.

(21) Appl. No.: 12/057,656

(22) Filed: Mar. 28, 2008

(65) Prior Publication Data

US 2008/0243073 A1    Oct. 2, 2008

(30) Foreign Application Priority Data

Mar. 30, 2007    (CN) .................. 2007 1 0090989

(51) Int. Cl.
*A61M 5/00* (2006.01)
(52) U.S. Cl. ..................................... 604/110
(58) Field of Classification Search .............. 604/110
See application file for complete search history.

(56) References Cited

U.S. PATENT DOCUMENTS 5,578,015 A * 11/1996 Robb .................. 604/195

6,206,857 B1    3/2001 Chen
2004/0215150 A1    10/2004 Shue et al.

FOREIGN PATENT DOCUMENTS

| EP | 1 716 880 A2 | 11/2006 |
| EP | 1716880 | * 11/2006 |
| WO | 99/53979 A1 | 10/1999 |
| WO | 2005/058398 A1 | 6/2005 |

OTHER PUBLICATIONS

EP Search Report dated Jul. 7, 2008 issued in EP Application No. 08005025.5.

* cited by examiner

*Primary Examiner*—Nicholas D Lucchesi
*Assistant Examiner*—Diva Ranade
(74) *Attorney, Agent, or Firm*—Sughrue Mion, PLLC

(57) ABSTRACT

The present invention provides an improved barrel type plunger for use with needle-retractable safety syringes. The plunger includes a barrel, a needle retracted trigger and a supporting member. A front portion of the barrel is fitted over a sealing rubber pad, a slotted hole is provided at a wall of the front portion of said barrel, a bearing piece is provided in the slotted hole, and one end of the bearing piece is connected to the front side wall of the slotted hole. The supporting member is releasably engaged in the barrel. After having released from the barrel, the supporting member is able to translate backwards under the action of a needle retraction force so that the bearing piece can be returned to such a position that the needle can be retracted backwards to the interior of the barrel.

22 Claims, 11 Drawing Sheets

BARREL TYPE PLUNGER FOR USE WITH A NEEDLE-RETRACTABLE SAFETY SYRINGE AND THE SYRINGE USING THE SAME

TECHNICAL FIELD

The present invention relates to a medical instrument, particularly to an improved barrel type plunger for use with a needle-retractable safety syringe and a syringe containing the above-mentioned barrel type plunger.

BACKGROUND ART

Syringes are commonly and largely used in the field of medical treatment. If the syringes are used repeatedly, it is likely to cause the diseases to spread among the different patients and result in cross infection which will endanger the health of the public people. In order to seek illegal gains, some persons collect the used and discard disposable syringes and put these syringes into the medical treatment market again. As a result, it will be a heavy threaten of spreading and proliferating many diseases. On the other hand, healthcare workers and the waste collecting persons may suffer from needlesticks after the completion of injection because of the expose of the needle heads so as to cause disease infections or spread.

In order to prevent repeatedly using the syringes and to make the syringes self-destruct immediately once they have been used so that the syringes can actually be used only one time and accidental needlesticks caused by the used syringes can be prevented from occurring, a solution concerning a needle-retractable disposable syringe has been proposed. Also, an improvement on the barrel type plunger used for this kind of syringe has been made so that the self-destruction of the syringes and the controllability of the needle retraction can be obtained.

As an example, Chinese utility model patent ZL200520015704.2 discloses a novel barrel type plunger used for a needle-retractable safety syringe and a safety syringe using with the same. As described in this Chinese patent, the bearing piece is controlled by the fitting of the outer barrel and the inner barrel of the barrel type plunger, and the bearing piece is used to control the retraction of the pushing post and the released needle carrier. In this way, the self-destruction of the syringes after the completion of injection and the controllability of the needle retraction can be realized. Moreover, it can prevent the syringes from being used repeatedly, and can eliminate a risk of accidental needlesticks caused by the exposed syringes needle after the completion of injection.

Although the solution as disclosed in the above-mentioned Chinese utility model patent can realize the controllability of the syringe needle retraction after the injection, this solution has the following defects: (1) the structure of the barrel type plunger is relatively complex so that it is rather difficult for the barrel type plunger to be produced and the assembling procedure is relatively complex, thereby the production cost is relatively high; (2) since the structure of the barrel type plunger is relatively complex, it is hardly to be suitable for a syringe having minor milliliter volume, such as 1 ml syringe.

DISCLOSURE OF THE INVENTION

In order to overcome the above-mentioned disadvantages present in the prior art, an object of the present invention is to provide a barrel type plunger which has simple structure, is easy to produce and assemble, and can make a needle to be retracted under the control. Another object of the present invention is to provide a syringe equipped with the above-mentioned barrel type plunger.

According to one respect of the invention, the present invention provides an improved barrel type plunger for use with a needle-retractable safety syringe, comprising a barrel, a needle retracted trigger and a supporting member, a front portion of said barrel is fitted with a sealing rubber pad, wherein a slotted hole is provided at a wall of the front portion of said barrel, a bearing piece is provided in said slotted hole, one end of said bearing piece is connected to the front side wall of said slotted hole; during the assembly, said bearing piece is deflected laterally towards the interior of said barrel in a resettable manner in order to support said needle retracted trigger; said needle retracted trigger is provided at a front end of a cavity of said barrel and is supported on said bearing piece which has been deflected laterally; said supporting member is provided in said barrel, the front end of which supports said bearing piece which has been deflected laterally, and the rear end of which is provided with a base for sealing the opening at the rear end of said barrel; said barrel and said supporting member are provided with a snap-in structure respectively, which can be engaged cooperatively with each other; during the assembly, said supporting member is releasably engaged in said barrel; and after having released from said barrel, said supporting member is able to translate backwards under the action of a needle retraction force so that said bearing piece can be returned to such a position that said needle retracted trigger and said needle can be retracted backwards to the interior of said barrel.

In a preferable embodiment of the present invention, said needle retracted trigger is a pushing post having a closed front portion; after the assembly, the front end of said pushing post is projected beyond an opening of the barrel cavity formed at the front end of said barrel and said sealing rubber pad, and the projected portion is in a shape of a tubular structure with a flush end or in a shape of a tubular structure having an end with longitudinally extending gear-like projections.

In another exemplary embodiment of the invention, said supporting member is in a shape of barrel body having an opened front end and a closed rear end, the wall of the rear portion of said barrel body is disposed with at least one opening, a flexible rib extends forwardly along the axial direction of said barrel body from the rear inner wall each said opening, an outer wall of said flexible rib is formed with a first projection which is in a shape of semi-sphere, triangle or other shapes having a slanted top end surface; the wall of said barrel is provided with a window at a position which corresponds to the position of said first projection; and during the assembly, said first projection is supported at the rear edge of said window and is projecting beyond said window so that said supporting member can be releasably engaged with said barrel.

In a further exemplary embodiment of the invention, a notch adapted for restoring said bearing piece is formed on the wall of the front end portion of said supporting member at a position corresponding to the home position of said bearing piece; and said openings and said windows are in a number of two and are disposed opposite to each other, each of said openings has a flexible rib therein, one first projection is provide on the outer wall of each of said flexible ribs at the same level.

In a further exemplary embodiment of the invention, said slotted hole provided on the wall of the front portion of said barrel extends toward the middle-rear part of said barrel, and an slotted hole is formed on the wall of said barrel opposed to said slotted hole; said supporting member includes the base, two flexible ribs and two first projections, said two flexible ribs are disposed oppositely on the front end surface of said base and is extending forwardly along the axial direction of said barrel, the arrangement of said flexible ribs are set in such a manner that said flexible ribs can be engaged with said two slotted holes, respectively, said two first projections are provided on the outer walls of said two flexible ribs, respectively, and are in a shape of semi-sphere, triangle or other shapes having a slanted top end surface; during the assembly, said two first projections are supported at the rear edge of said two slotted holes, respectively, and are projecting beyond said slotted holes so that said supporting member can be releasably engaged in said barrel; and said bearing piece is supported by the front end of at least one of said flexible ribs after it has been deflected laterally.

In a further preferably embodiment of the invention, on the wall of the middle-rear part of said barrel is provided with two opposed windows; said supporting member includes the base, two flexible ribs and a supporting bar, said flexible ribs and the supporting bar are all disposed on the front end surface of said base and extend forwardly along the axial direction of said barrel, the outer walls of said two flexible ribs are provided with a first projection, respectively, which is in a shape of semi-sphere, triangle or other shapes having a slanted top end surface, the length of said supporting bar is suitable to a position where said bearing piece is in the cavity of the barrel after it has been deflected laterally, the arrangement orientation of the supporting bar on the base is set to match to the arrangement orientation of said bearing piece so that said bearing piece is supported by the front end of said supporting bar after it has been deflected laterally; and during the assembly, said first projections are supported at the rear edges of said windows and are projecting beyond said windows so that said supporting member can be releasably engaged in said barrel.

In a further preferably embodiment of the invention, a projected retaining ring is provided in a circle along the inner wall of the rear portion of said barrel so that said supporting member will be blocked by said retaining ring again after it has been moved backwards to such an extent that said bearing piece has returned to its home position.

In a further preferably embodiment of the invention, the outer wall of said flexible rib is further provided with a second projection thereon, which is arranged behind said first projection, the distance between the rear end surface of said first projection and the rear end surface of said second projection is set to be equal to or larger than the backward movement distance of said supporting member required for returning said bearing piece to the position where said pushing post and the needle can be retracted back to the interior of said barrel, and the projecting height of said second projection is set to be smaller than or equal to the projecting height of said first projection; and during the assembly, said first projection and said second projection are mounted in the window and extend beyond the same, said second projection is supported by the rear edge of said window so that said supporting member can be releasably engaged in said barrel.

In a further preferably embodiment of the invention, at least one window is formed on the wall of the middle-rear part of said barrel; said supporting member is in a shape of barrel body having an opened front end and a closed rear end, the opening is formed on the wall of the middle-rear portion of said barrel body at a position corresponding to the position of each of window, a flexible rib extending backwards along the axial direction of said barrel body are formed on the front side wall of said opening, an outer wall of said flexible rib is formed with a first projection thereon, which is in a shape of semi-sphere, triangle or other shapes having a slanted top end surface; and during the assembly, said first projection (601) is supported at the rear edge of said window and is projecting beyond said window so that said supporting member can be releasably engaged with said barrel.

In a further preferably embodiment of the invention, a notch adapted for restoring said bearing piece is provided on the wall of the front end portion of said barrel-like supporting member at a position corresponding to the home position of said bearing piece, the windows formed on the wall of said barrel and the openings on the wall of said barrel-like supporting member are in a number of two and are substantially symmetrical, respectively, said flexible bars and said first projections provided thereon are in two sets and are substantially symmetrical, respectively; each of said flexible bar is further provided with a second projection thereon, which is arranged behind said first projection, the distance between the rear end surface of said first projection and the rear end surface of said second projection is set to be equal to or larger than the backward movement distance of said barrel-like supporting member required for returning said bearing piece to the position where said pushing post and the needle can be retracted back to the interior of said barrel, and the projection height of said second projection is set to be smaller than or equal to the projection height of said first projection; and during the assembly, said first projection and said second projection are all mounted in the window and extend beyond the same, said second projection is supported by the rear edge of said window so that said supporting member can be releasably engaged in said barrel.

In a further preferably embodiment of the invention, said supporting member is composed of a front barrel and a rear barrel which are nested one on the top of another; a notch adapted for restoring said bearing piece is formed on the wall of a front end portion of said front barrel at a position which corresponds to the home position of said bearing piece, the rear end of said front barrel and the front end of said rear barrel are provided with a socket and spigot joint, respectively, which can be engaged to each other; said opening is formed on the wall of said rear barrel behind the portion which is jointed to said front barrel.

In a further preferably embodiment of the invention, the outer diameter of the portion at the front end of said rear barrel which is joined to said front barrel is set to be smaller than the outer diameter of the other portions of said rear barrel and match to the inner diameter of said front barrel, a set piece is disposed on a portion at the front end of said rear barrel which is joined to said front barrel; a locating slot or locating hole adapted for fitting to said set piece is formed on the wall of the rear end portion of said front barrel at a portion which is joined to said rear barrel; a second projection is formed behind said first projection, the projecting height of said first projection is set to be larger than or equal to the projecting height of said second projection, and the distance between the rear end surface of said first projection and the rear end surface of said second projection is set to be equal to or larger than the backward movement distance of said supporting member required for returning said bearing piece to the position where said pushing post and the needle can be retracted back to the interior of said barrel; and during the assembly, said first projection and said second projection are all mounted in the window and extend beyond the same, said second projection is supported by the rear edge of said window so that said supporting member can be releasably engaged in said barrel.

In a further preferably embodiment of the invention, the barrel type plunger for use with a needle-retractable safety syringe further comprises a protective sleeve, said protective sleeve includes a thicker tubing and a thinner tubing which are connected together; the inner diameter of said thicker tubing is set to be larger than or equal to the outer diameter of the barrel of the syringe; a flange is formed in a circle on the outer wall of the rear portion of said barrel; the inner diameter of said thinner tubing is set to match to the outer diameter of said barrel, and a recess which can be engaged to said flange is formed in a circle on the inner wall of said thinner tubing; and during the assembly, said protective sleeve is fitted to the rear end of said barrel and is secured thereon by means of the engagement of said recess and said flange so that the thicker tubing surrounds the engaged portion where said barrel and said supporting member are engaged to each other.

In a further preferably embodiment of the invention, the barrel type plunger for use with a needle-retractable safety syringe further comprises a sealing pad and a compressible needle stop member, said sealing pad is mounted between the walls of said pushing post and the front end of said barrel; the front portion of said pushing post is provided with a chamber, in which said needle stop member is disposed, the leading end of said needle stop member projects beyond the front end of said pushing post after it has blocked the opening of the chamber of said pushing post.

In a further preferably embodiment of the invention, a tubular front end portion with a flush end or with an end having longitudinally extending gear-like protrusions is exposed after said barrel is fitted with said sealing rubber pad; said pushing post can be replaced with a compressible needle stop member which includes a stop post and a spring fitted over the rear portion of said stop post and supporting said stop post; the cavity provided at the front end of said barrel for arranging said needle stop member includes a front chamber and a rear chamber, the inner diameter of said front chamber is set to match to the outer diameter of said stop post, and the inner diameter of said rear chamber is set to be larger than the outer diameter of said stop post; a recess is formed in a circle on the portion of said stop post corresponding said front chamber, a sealing ring is disposed in said recess, a projected orientation ring is formed in at least one circle on such a portion of said stop post corresponding to said rear chamber, the outer diameter of said orientation ring is set to match to the inner diameter of said rear chamber; the leading end of said needle stop member projects out of the front end of said barrel after it has blocked the opening at the front end of said barrel, and the rear end of said needle stop member can be compressed and is supported on said bearing piece; the front end surface of said stop post is provided with a recess; and the wall of the tubular front end portion of said barrel (1) is also provided with a slot which can be communicated with said recess.

In a further preferably embodiment of the invention, said needle retracted trigger can be replaced with a needle carrying member, a tubular front end portion with a flush end or with an end having longitudinally extending gear-like protrusions is exposed after said barrel is fitted with said sealing rubber pad to activate the needle in order to make it be retracted.

According to another aspect of the invention, the present invention provides a needle-retracted controlled safety syringe which comprises a syringe barrel, a needle carrier carrying a needle, a sleeve for covering said needle carrier, a spring, an O-ring and a plunger, wherein a shoulder is formed at the front end of said syringe barrel and is shrunk toward the axial direction of said syringe barrel, a bushing extends forwardly from said shoulder, a flange is formed on a portion of the inner wall of said bushing which is connected to said shoulder, and a snap-on, plug-connected or screw connection structure is provided on the outer wall of said bushing; said needle carrier is of a tubular body having a through hole provided at its centre securing a needle therein, a flaring base is provided at the rear end of said needle carrier, said needle carrier is mounted on the inside of said bushing; said O-ring is arranged on a narrower portion of said flaring base of said needle carrier and is fitted with said flange provided at the inner wall of said bushing so that said needle carrier can be detachably mounted in said bushing; said spring is fitted over said needle carrier, and its rear end is supported on said flaring base of said needle carrier; said sleeve for covering said needle carrier has a cavity opened backwards, the inner diameter of which is set to match to the outer diameter of said bushing, and the inner wall of said sleeve for covering said needle carrier is provided with a snap-on, plug-connected or screw connection structure which can be engaged with said snap-on, plug-connected or screw connection structure provided on the outer wall of said bushing, the closed front end of said sleeve for covering said needle carrier is provided with a needle hole, when said sleeve for covering said needle carrier is snapped, plugged or screwed on said bushing mounted with said needle carrier, the head of said needle can project out of said needle hole, the closed front end of said sleeve for covering said needle carrier can press against the leading end of said spring and pre-compress said spring between said closed front end and said flaring base of said needle carrier; said barrel-like plunger is mounted in said syringe barrel, and when said barrel-like plunger is pushed to the end of a cavity of said syringe barrel, a pushing post or a tubular front end portion of a barrel of said barrel-like plunger urges said O-ring to move entirely or partly so that the fixation of said needle carrier and said bushing is relieved, while the rear end of said syringe barrel relieves the engagement between a supporting member and said barrel present in said barrel-like plunger and releases said supporting member.

As an improvement of the present invention, the needle-retracted controlled safety syringe of the invention comprises a syringe barrel, a needle carrier carrying a needle, a sleeve for covering said needle carrier, a spring, an O-ring and a plunger, wherein a shoulder is formed at the front end of said syringe barrel and is shrunk toward the axial direction of said syringe barrel, a bushing extends forwardly from said shoulder; said needle carrier is of a tubular body having a through hole provided at its centre and securing a needle therein, a flaring base is provided at the rear end of said needle carrier; said sleeve for covering said needle carrier includes a first sleeve which has a closed front end and is provided with a needle hole and a second sleeve, the inner wall of the rear end portion of the second sleeve is provided with a flange, said first sleeve and said second sleeve can be connected as an entirety by means of screw connection, plugging or snapping-in or be connected fixedly by means of adhering or ultrasonic welding; said O-ring is arranged on a narrower portion of said flaring base of said needle carrier and is fitted with said flange provided at the inner wall of said rear end portion of said second sleeve so that said needle carrier can be detachably mounted in said sleeve for covering said needle carrier; said spring is fitted over said needle carrier, and its rear end is supported on said flaring base of said needle carrier; said needle carrier is mounted in said sleeve for covering said needle carrier, the head of said needle can project out of said needle hole formed at the front end of said first sleeve, the closed front end of said first sleeve presses against the leading end of said spring and pre-compresses said spring between said closed front end and said flaring base of said needle carrier; said sleeve for covering said needle carrier is detachably connected to said bushing of said syringe barrel by means of snapping-on, plugging or screw connection; said barrel-like plunger is mounted in said syringe barrel, and when said barrel-like plunger is pushed to the end of a cavity of said syringe barrel, a pushing post or a tubular front end portion of a barrel of said barrel-like plunger urges said O-ring to move entirely or partly so that the fixation of said needle carrier and said sleeve for covering said needle carrier is relieved, while the rear end of said syringe barrel relieves the engagement between a supporting member and said barrel present in said detached barrel-like plunger and releases said supporting member.

As a preferable embodiment of the needle-retracted controlled safety syringe of the invention, the needle hole at the front end of said first sleeve or the needle hole at the front end of said sleeve has an inward flared structure, the front portion of said needle carrier is also provided with a cone-shaped structure, the shape of which matches to the above-mentioned inward flared structure; after the assembly, said needle carrier is fixed by the cooperation between the flared structure of said needle hole and said cone-shaped structure provided at the front portion of said needle carrier.

Compared to the prior art, the present invention presents the following remarkable and advantageous technical effects:

1. The improved barrel type plunger for use with a needle-retractable safety syringe and the needle-retracted controlled safety syringe containing the above-mentioned barrel type plunger according to the present invention have simper and more reasonable structure, are easy to produce and assemble and can make the controllable retraction of the needle even more convenient.

2. The improved barrel type plunger for use with a needle-retractable safety syringe and the needle-retracted controlled safety syringe containing the above-mentioned barrel type plunger according to the present invention have a even more compact structure so that they can be used for minor milliliter volume syringes having a relatively thinner syringe barrel.

BRIEF DESCRIPTION OF DRAWINGS

Various exemplary embodiments of the invention will be described in detail with reference to the following figures, wherein:

FIG. 15-1 is a perspective view of the supporting member of the barrel type plunger according to the embodiment 8 of the present invention;

FIG. 16-1 is a perspective view of the barrel of the barrel type plunger according to the embodiment of the present invention;

BEST MODES FOR CARRYING OUT THE INVENTION

Embodiment 1

Figure 1:
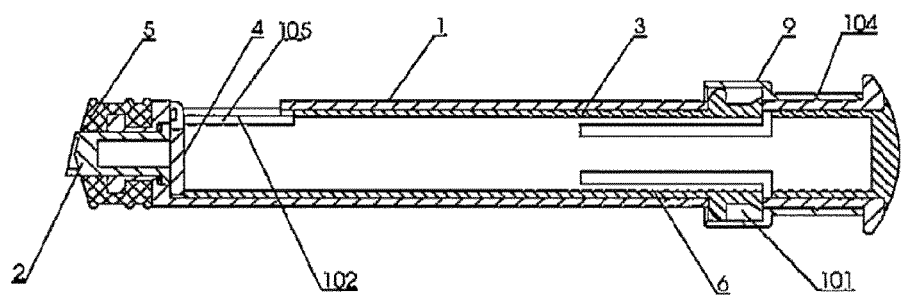
FIG. 1 is a cross sectional view of the improved barrel type plunger for use with a needle-retractable safety syringe according to the embodiment 1 of the present invention.

As shown in FIGS. 1, 2, 9 10 and 17, the improved barrel type plunger for use with a needle-retractable safety syringe according to the embodiment 1 comprises a barrel 1, a needle retracted trigger and a supporting member 3. A head portion of the barrel 1 is fitted with a sealing rubber pad 5.

The needle retracted trigger is a pushing post 2 having a closed front portion. After the assembly, the front end of the pushing post 2 is projected beyond an opening of the barrel cavity formed at the front end of said barrel 1 and the sealing rubber pad 5. Also, the projected portion is in a shape of a tubular structure with a flush end or in a shape of a tubular structure having an end with longitudinally extending gear-like projections.

A slotted hole 102 is provided at a wall of the front portion of said barrel 1. In the slotted hole 102, a bearing piece 4 is provided therein, one end of which is connected to the front side wall of said slotted hole 102. During the assembly, said bearing piece 4 is deflected laterally towards the interior of said barrel 1 in a resettable manner in order to support the needle retracted trigger. The rear portion of the barrel 1 is provided with two opposed windows 101. A flange 104 is formed in a circle on the outer wall of the rear portion of the barrel 1.

The pushing post 2 is provided at a front end of the cavity of the barrel 1 and is supported on the bearing piece 4 which has been deflected laterally.

The supporting member 3 is of a barrel body and is provided in the barrel 1. The front end of the supporting member 3 supports the bearing piece 4 which has been deflected laterally, and the rear end of it is provided with a sealing base 301 for sealing the opening at the rear end of the barrel 1.

A notch 105 adapted for restoring the bearing piece 4 is formed on the wall of the front end portion of the supporting member 3 at a position corresponding to the home position of the bearing piece 4.

On the wall of the rear portion of the supporting member 3, two opposed openings 302 are formed at the positions which correspond to the positions of windows 101, respectively. A flexible rib 6 extending backwards along the axial direction of said barrel body is disposed at the front side wall of each of the openings 302.

The flexible rib 6 is provided with a first projection 601 and a second projection 602 along its length direction. The first projection 601 is in a shape of a block body with a slanted surface formed at its top portion. The second projection 602 is in a shape of triangle.

The distance between the rear end surface of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. Moreover, the projecting height of the second projection 602 is set to be smaller than or equal to the projecting height of the first projection 601. During the assembly, the first projection 601 and the second projection 602 are mounted in the window 101 and extend beyond the same, and the second projection 602 is supported by the rear edge of the window 101. As a result, the supporting member 3 can be releasably engaged in the barrel 1.

Said barrel type plunger also comprises a protective sleeve 9 including a thicker tubing 901 and a thinner tubing 902 which are connected together. The inner diameter of the thicker tubing 901 is set to be larger than or equal to the outer diameter of the syringe barrel of the syringe. The inner diameter of the thinner tubing 902 is set to match to the outer diameter of the barrel 1. A recess 903 which can be engaged to the flange 104 formed at the rear portion of barrel 1 is formed in a circle on the inner wall of the thinner tubing 902. The protective sleeve 9 can be fitted to the rear end of the barrel 1 and can be secured thereon through the engagement of the recess 903 and the flange 104 so that the thicker tubing 901 can surround the first projection 601 and the second projection 602 provided on the flexible rib 6 in order to prevent the barrel type plunger from self-destructing before the use due to the misoperation.

In the present embodiment, the bearing piece 4 provided at the front side wall of the slotted hole 102 may also be made from a part of the wall of the front portion of the barrel 1.

Embodiment 2

As shown in FIGS. 1, 2, 7, 8 and 17, the barrel type plunger for use with the needle-retractable safety syringe according to the present embodiment is substantially the same as that of embodiment 1. The differences between the embodiments 1 and 2 only lie in that, in the present embodiment, there only is one window 101 provided on the wall of the barrel 1 and one opening 302 provided on the wall of the barrel-like supporting member 3, respectively, and there also only is one flexible rib 6.

Embodiment 3

As shown in FIGS. 2, 3, 4 and 17, the barrel type plunger for use with the needle-retractable safety syringe according to the present embodiment is substantially the same as that of embodiment 1. The differences between the embodiments 3 and 1 lie in that, in the present embodiment, there only is one window 101 provided on the wall of the barrel 1 and one opening 302 provided on the wall of the barrel-like supporting member 3, respectively, and there also only is one flexible rib 6. In addition, only a first projection is provided on the flexible rib 6.

The supporting member 3 is in a shape of a barrel body having an opened front end and a closed rear end. On the wall of the rear portion of the barrel body, a opening 302 is disposed. A flexible rib 6 extending forwardly along the axial direction of said barrel body is formed on the rear inner wall of the opening 302. On the outer wall of the flexible rib (6), a first projection 601 is formed in a shape of a block body. A window 101 is provided on the wall of the barrel 1 at a position which corresponds to the position of the first projection 601. During the assembly, the first projection 601 is supported at the rear edge of said window 101 and is projecting beyond the window 101 so that the supporting member 3 can be releasably engaged with said barrel 1.

Figure 28:
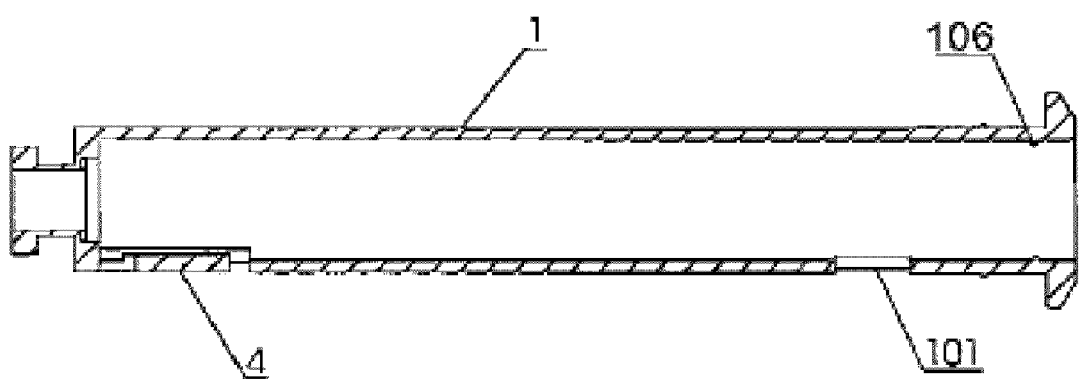
FIG. 28 is a cross sectional view of the barrel of the barrel type plunger according to an embodiment of the present invention.

A projected retaining ring 106 (in FIG. 28) is provided in a circle along the inner wall of the rear portion of the barrel 1 so that the supporting member 3 will be blocked by said retaining ring again after it has been moved backwards to such an extent that said bearing piece 4 has returned to its home position.

In the present embodiment, the first projection 601 can be in a shape of semi-sphere, triangle or any other shape having a slanted top end surface.

Embodiment 4

As shown in FIGS. 1, 2, 5 and 17, the barrel type plunger for use with the needle-retractable safety syringe according to the present embodiment is substantially the same as that of embodiment 3. The differences between the embodiments 3 and 4 lie in the following features:

The outer wall of the flexible rib 6 is further provided with a second projection 602 thereon, which is provided behind the first projection 601. The distance from the rear end surface of the second projection 602 to the rear end surface of the first projection 601 is set to be equal to or larger than the backward movement distance of the supporting member 3 required for returning the bearing piece 4 to the position where the pushing post 2 and the needle can be retracted back to the interior of said barrel 1. In addition, the projecting height of the second projection 602 is set to be smaller than or equal to the projecting height of the first projection 601. During the assembly, the first projection 601 and the second projection 602 are mounted in the window 101 and extend beyond the same, and the second projection 602 is supported by the rear edge of the window 101 so that the supporting member 3 can be releasably engaged in the barrel 1.

Embodiment 5

As shown in FIGS. 1, 2, 6 and 17, the barrel type plunger for use with the needle-retractable safety syringe according to the present embodiment is substantially the same as that of embodiment 3. The differences between the embodiments 3 and 5 lie in the following features:

The supporting member 3 is in a shape of a barrel body. Two opposed openings 302 are formed on the wall of the rear portion of the supporting member 3. A flexible rib 6 extending forwardly along the axial direction of said barrel body is disposed at the rear side wall of each of the openings 302.

Embodiment 6

Figure 11:
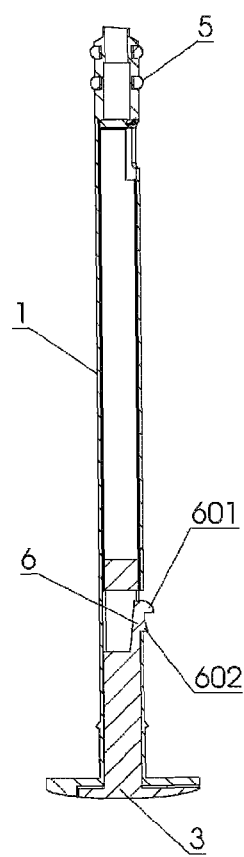
FIG. 11 a cross sectional view of the barrel type plunger according to the embodiment 6 of the present invention.
Figure 12:
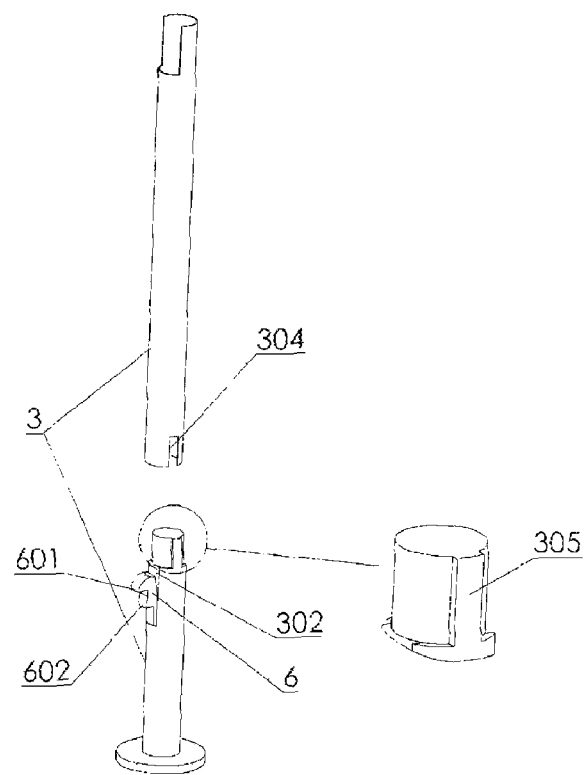
FIG. 12 is a perspective view of the supporting member of the barrel type plunger according to the embodiment 6 of the present invention.

As shown in FIGS. 11 and 12, the barrel type plunger for use with a needle-retractable safety syringe according to the present embodiment comprises a barrel 1, a pushing post 2 and a supporting member 3. The head portion of the barrel 1 is fitted with a sealing rubber pad 5. The structures of the barrel 1, the pushing post 2 and the sealing rubber pad 5 are the same as those of the respective parts of embodiment 4.

The supporting member 3 is composed of a front barrel and a rear barrel which are nested one on the top of another. A notch adapted for restoring the bearing piece 4 is formed on the wall of a front end portion of said front barrel at a position which corresponds to the home position of the bearing piece 4. Additionally, the rear end of said front barrel and the front end of said rear barrel are provided with a socket and spigot joint, respectively, which can be engaged to each other.

A opening 302 is formed on the wall of said rear barrel behind the portion which is jointed to said front barrel. A flexible rib 6 extending backwards along the axial direction of said barrel body is disposed at the front side wall of the opening 302.

The outer diameter of the portion of the front end of said rear barrel which is joined to said front barrel is set to be smaller than the outer diameter of the other portions of said rear barrel and match to the inner diameter of said front barrel. A set piece 305 is disposed on the portion at the front end of said rear barrel which is joined to said front barrel. A locating slot or locating hole 304 adapted for fitting to the set piece 305 is formed on the wall of the portion at the rear end of said front barrel which is joined to said rear barrel.

The flexible rib 6 is provided on its outer wall with a first projection 601 and a second projection 602 which is provided behind the first projection 601. The projecting height of the first projection 601 is set to be larger than or equal to the projecting height of the second projection 602, and the distance between the rear end surface of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. During the assembly, the first projection 601 and the second projection 602 are all mounted in the window 101 and extend beyond the same, and the second projection 602 is supported by the rear edge of the window 101. As a result, the supporting member 3 can be releasably engaged in the barrel 1.

The barrel type plunger according to the present embodiment has more compact structure and therefor is suitable to the minor milliliter volume syringes having a relatively thinner syringe barrel.

Embodiment 7

Figure 13:
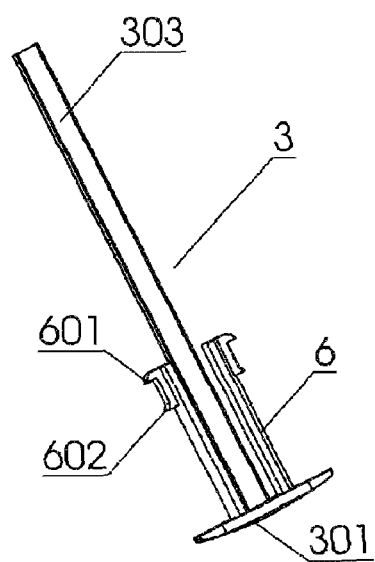
FIG. 13 is a cross sectional view of the supporting member of the barrel type plunger according to the embodiment 7 of the present invention.
Figure 14:
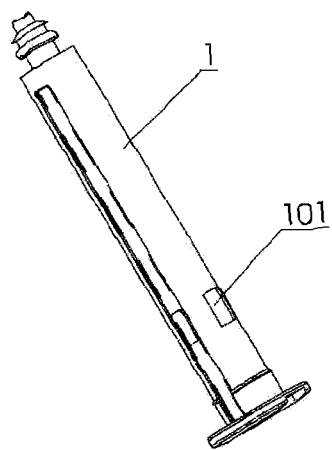
FIG. 14 is a perspective view of the barrel of the barrel type plunger according to the embodiment 7 of the present invention.

As shown in FIGS. 13 and 14, the barrel type plunger for use with the needle-retractable safety syringe according to the present embodiment is substantially the same as that of embodiment 1. The differences between the embodiments 1 and 7 lie in the following features:

The supporting member 3 includes a base 301, two flexible ribs 6 and a supporting bar 303.

The length of the supporting bar 303 is suitable to a position where the bearing piece 4 is in the cavity of the barrel 1 after it has been deflected laterally. The arrangement orientation of the supporting bar 303 on the base 301 is set to match to the arrangement orientation of the bearing piece 4.

On the outer walls of the flexible ribs 6, a first projection 601 is provided, which is in a shape of a block body and has a slanted surface at its top portion. Further, a second projection 602 is provided on the outer walls of the flexible ribs behind the first projection 601. The distance between the rear end of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. The projecting height of the second projection 602 is set to be smaller than or equal to the projecting height of the first projection 601. The first projection 601 and the second projection 602 are all mounted in the windows 101 and extend beyond the same, and the second projection 602 is supported by the rear edge of the window 101. As a result, the supporting member 3 can be releasably engaged in the barrel 1.

An elongated hole for receiving and locating the supporting bar 303 is provided at a portion of the barrel 1 at a position corresponding to the position of the supporting bar 303.

After being deflected laterally, the bearing piece 4 is supported by the front end of the supporting bar 303.

Embodiment 8

Figure 2:
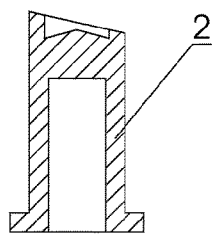
FIG. 2 is a cross sectional view of the pushing post of the barrel type plunger shown in FIG. 1.
Figure 3:
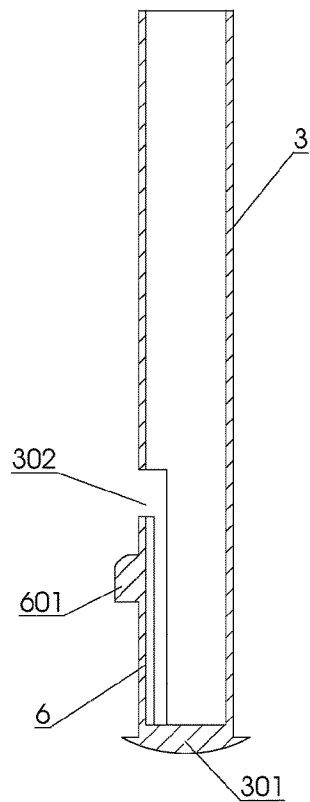
FIG. 3 is a cross sectional view of the supporting member of the barrel type plunger according to the embodiment 3 of the present invention.
Figure 4:
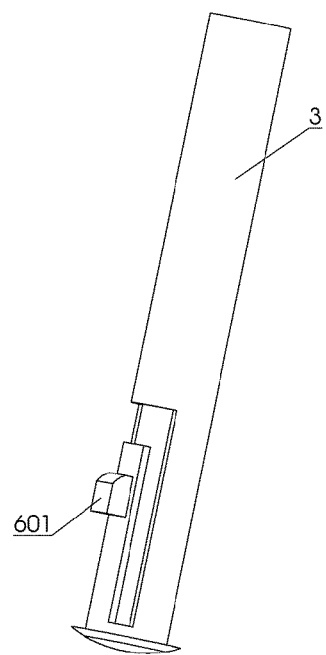
FIG. 4 is a perspective view of the supporting member of the barrel type plunger according to the embodiment 3 of the present invention.
Figure 5:
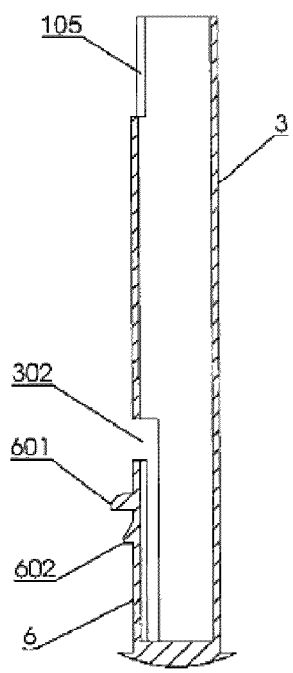
FIG. 5 is a cross sectional view of the supporting member of the barrel type plunger according to the embodiment 4 of the present invention.
Figure 6:
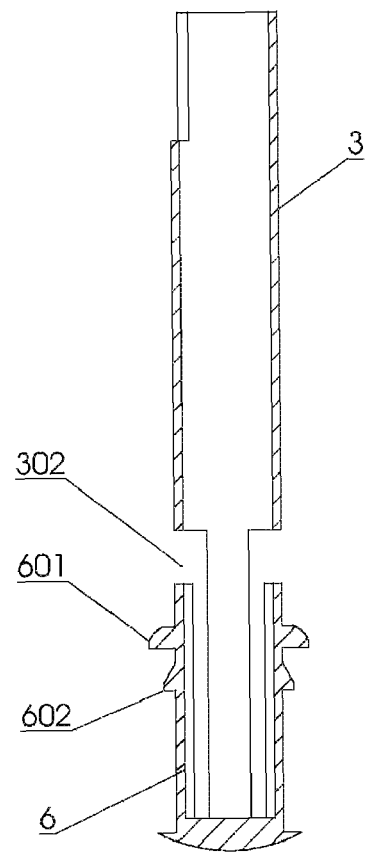
FIG. 6 is a cross sectional view of the supporting member of the barrel type plunger according to the embodiment 5 of the present invention.
Figure 7:
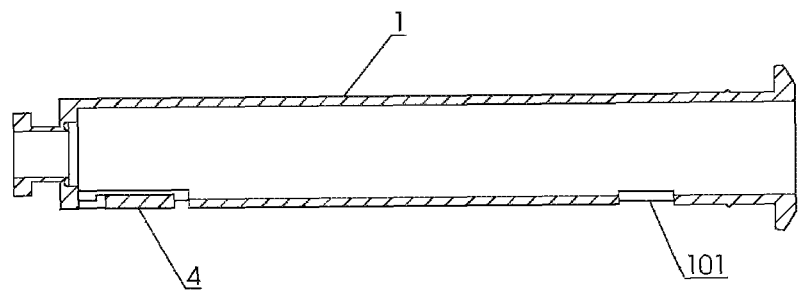
FIG. 7 is a cross sectional view of the barrel of the barrel type plunger according to the embodiment 2 of the present invention.
Figure 8:
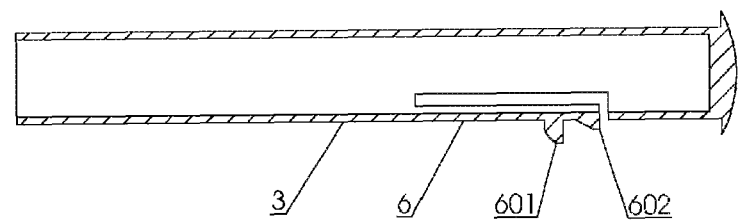
FIG. 8 is a cross sectional view of the supporting member of the barrel type plunger according to the embodiment 2 of the present invention.
Figure 9:
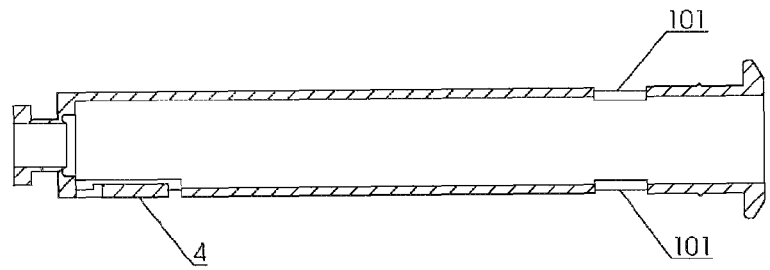
FIG. 9 is a cross sectional view of the barrel of the barrel type plunger according to the embodiments 1 and 9 of the present invention.
Figure 10:
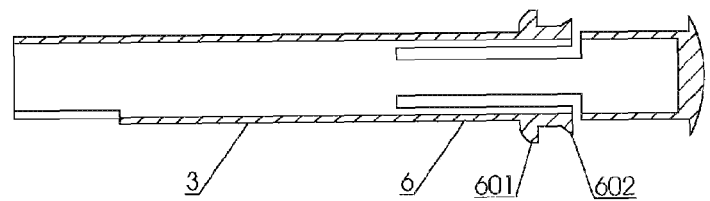
FIG. 10 is a cross sectional view of the supporting member of the barrel type plunger according to the embodiments 1 and 9 of the present invention.
Figure 15:
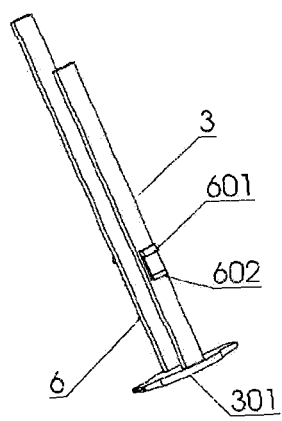
FIG. 15 is a perspective view of the supporting member of the barrel type plunger according to the embodiment 8 of the present invention.
Figures 1, 15:
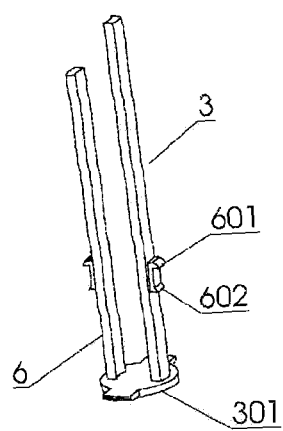
Figure 16:
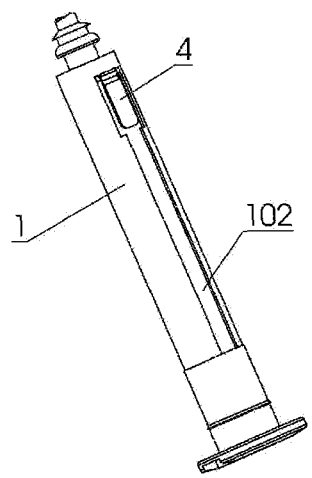
FIG. 16 is a perspective view of the barrel of the barrel type plunger according to the embodiment of the present invention.
Figures 1, 16:
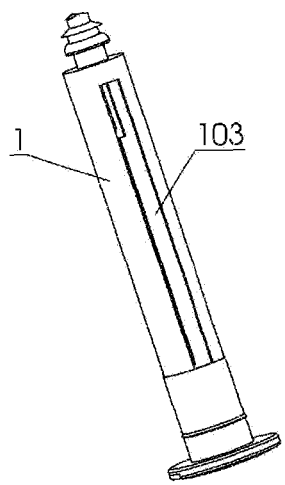

As shown in FIGS. 15, 15-1, 16 and 16-1, the barrel type plunger for use with the needle-retractable safety syringe according to the present embodiment is substantially the same as that of embodiment 7. The differences between the embodiments 7 and 8 lie in the following features:

The slotted hole 102 provided on the wall of the front portion of the barrel 1 extends toward the middle-rear part of the barrel 1. And, a slotted hole 103 is formed on the wall of the barrel 1 opposite to the slotted hole 102. The length of the slotted hole 103 may be set to be equal to that of the slotted hole 102 as shown in FIG. 15-1, or may not be set to be equal to that of the slotted hole 102 as shown in FIG. 15-2.

The supporting member 3 includes a base 301, two flexible ribs 6 and two first projections 601. The two flexible ribs 6 are disposed oppositely on the front end surface of the base 301 and extend forwardly along the axial direction of the barrel 1. The heights and positions of the flexible ribs 6 is set to match to the heights and positions of the slotted hole 102 and the slotted hole 103, respectively.

During the assembly, said two first projections 601 are supported at the respective rear edge of the two slotted holes 102,103, respectively, and are projecting beyond the slotted holes 102,103 so that the supporting member 3 can be releasably engaged in the barrel 1.

On the outer walls of each of the flexible ribs 6, a first projection 601 is provided. A second projection 602 is provided behind each of the first projections 601.

Each of the two first projections 601 is in a shape of a block body and has a slanted surface at its top portion. Further, the shape of each of the second projections 602 is triangular.

The distance between the rear end surface of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. The projecting height of the second projection 602 is set to be smaller than or equal to the projecting height of the first projection 601. During the assembly, the first projection 601 and the second projection 602 are all mounted in the slotted hole 102 and extend beyond the same, and the second projection 602 is supported by the rear edge of the window 101. As a result, the supporting member 3 can be releasably engaged in the barrel 1.

After being deflected laterally, the bearing piece 4 is supported by the front end of at least one of the flexible ribs.

Embodiment 9

As shown in FIGS. 9, 10, 17, 18 and 21, the barrel type plunger for use with the needle-retractable safety syringe according to the present embodiment is substantially the same as that of embodiment 1. The differences between the embodiments 1 and 9 lie in the following features:

The front portion of the pushing post 2 is provided with a chamber, in which a compressible needle stop member 11 is disposed. The leading end of the needle stop member 11 projects beyond the front end of the pushing post 2 after it has blocked the opening of the chamber of the pushing post 2.

A sealing pad 10 is further arranged between the respective walls of the pushing post 2 and the front end of the barrel 1.

Embodiment 10

Figure 17:
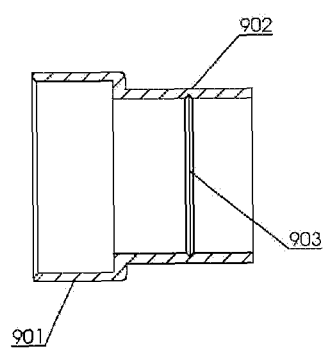
FIG. 17 is a cross sectional view of the protective sleeve according to the various embodiments of the present invention, respectively.
Figure 18:
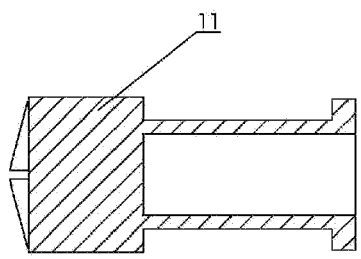
FIG. 18 is a cross sectional view of the needle stop member of the barrel type plunger according to the embodiment 9 of the present invention.
Figure 19:
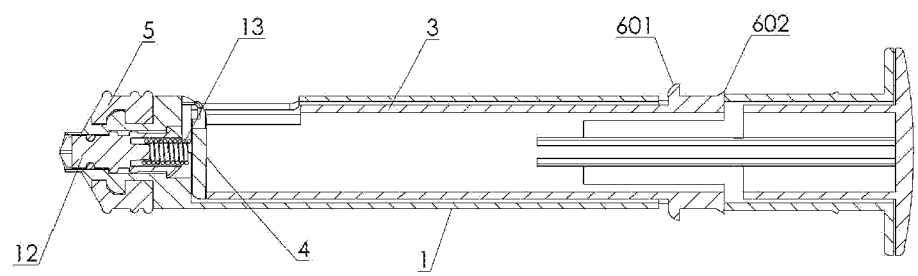
FIG. 19 is a cross sectional view of the barrel type plunger according to the embodiment 10 of the present invention.
Figure 20:
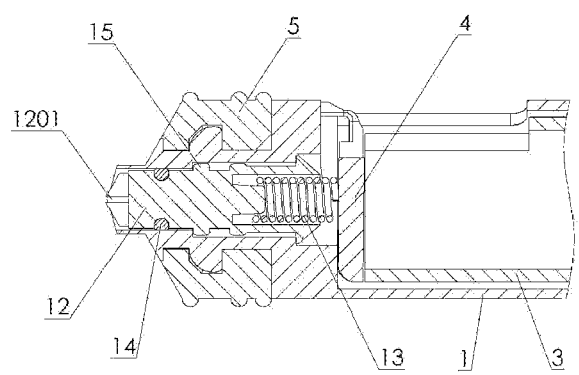
FIG. 20 is an enlarged cross sectional view of the front end of the barrel type plunger according to the embodiment 10 of the present invention.

As shown in FIGS. 17, 19 and 20, the barrel type plunger for use with the needle-retractable safety syringe according to the present embodiment is substantially the same as that of embodiment 9. The differences between the embodiments 9 and 10 lie in the following features:

A tubular front end portion with a flush end or an end having longitudinally extending gear-like protrusions is exposed after the barrel 1 is fitted with a sealing rubber pad 5. The above-mentioned tubular front end portion forms a needle retracted trigger.

The pushing post 2 further comprises a compressible needle stop member 11 which includes a stop post 12 and a spring 13 fitted over the rear portion of said stop post and supporting said stop post.

The cavity provided at the front end of the barrel 1 for arranging the needle stop member 11 includes a front chamber and a rear chamber. The inner diameter of the front chamber is set to match to the outer diameter of the stop post 12, and the inner diameter of the rear chamber is set to be larger than the outer diameter of the stop post 12.

A recess is formed in a circle on the portion of the stop post 12 at a position which corresponds to the position of said front chamber. A sealing ring 14 is disposed in said recess.

A projected orientation ring 15 is formed in at least one circle on a portion of the stop post 12 at such a position that corresponds to the position of said rear chamber. The outer diameter of the orientation ring 15 is set to match to the inner diameter of said rear chamber.

The front end surface of the stop post 12 is provided with a recess 1201. Furthermore, on the wall of the tubular front end portion of the barrel 1 is provided with a slot (not shown in the drawings) which can be communicated with the recess 1201. The leading end of the needle stop member 11 projects out of the front end of the barrel 1 after it has blocked the opening at the front end of the barrel 1. The rear end of the needle stop member 11 can be compressed and supported on the bearing piece 4.

Embodiment 11

The barrel type plunger for use with the needle-retractable safety syringe according to the present embodiment is substantially the same as that of embodiment 1. The differences between the embodiments 1 and 11 lie in the following features:

The needle retracted trigger can be replaced with a needle carrying member.

A tubular front end portion with a flush end or an end having longitudinally extending gear-like protrusions is exposed after the barrel 1 is fitted with the sealing rubber pad 5 in order to activate the needle and make the needle to be retracted. The needle carrying member for carrying the needle is provided in the cavity of the tubular front end portion.

Embodiment 12

Figure 21:
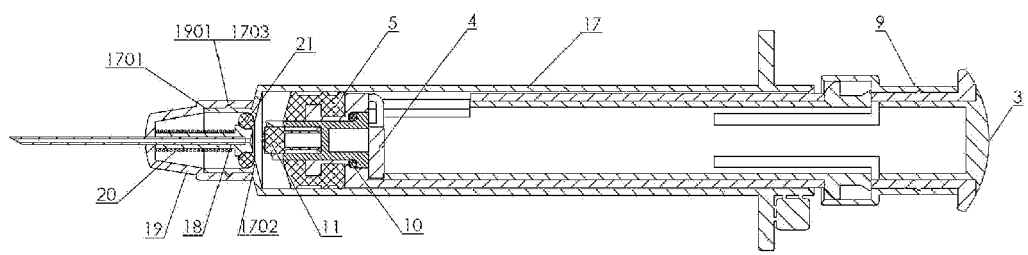
FIG. 21 is a cross sectional view showing the barrel type plunger according to the embodiment 9 of the present invention and the needle-retracted controlled safety syringe according to the embodiment 12 of the present invention.

As shown in FIG. 21, the present embodiment provides a needle-retracted controlled safety syringe which comprises a syringe barrel 17, a needle carrier 18 carrying a needle, a sleeve 19 for covering the needle carrier 18, a spring 20, an O-ring 21 and a barrel-like plunger.

A shoulder is formed at the front end of the syringe barrel 17 and is shrunk toward the axial direction of the syringe barrel 17. A bushing 1701 extends forwardly from said shoulder. A flange 1702 is provided at the inner wall of a portion of the bushing 1701 which is connected to said shoulder. Additionally, a flange 1703 which can be connected to the sleeve 19 for covering the needle carrier 18 is provided on the outer wall of the bushing 1701. The flange 1703 can be replaced with other snap-on, plug-connected or screw connection structure.

The needle carrier 18 is in a shape of a tubular body having a through hole provided at its centre. The needle is arranged in the through hole of the needle carrier 18. A flaring base is provided at the rear end of the needle carrier 18.

The O-ring 21 is arranged on a narrower portion of the flaring base of the needle carrier 18 and is fitted with the flange 1702 provided at the inner wall of the bushing 1701 so that the needle carrier 18 can be detachably mounted in the bushing 1701.

The spring 20 is fitted over the needle carrier 18, and its rear end is supported on the flaring base of the needle carrier 18.

The sleeve 19 for covering the needle carrier 18 has a cavity opened backwards, the inner diameter of which is set to match to the outer diameter of the bushing 1701. The inner wall of the sleeve 19 for covering said needle carrier is provided with a recess 1901 which can be engaged with the flange 1703 provided on the outer wall of the bushing 1701. When the flange 1703 is replaced with other snap-on, plug-connected or screw connection structure, the recess 1901 can be replaced with a snap-on, plug-connected or screw connection structure which can be engaged with the snap-on, plug-connected or screw connection structure that replaced the flange 1703. The closed front end of the sleeve 19 for covering said needle carrier is provided with a needle hole. When the sleeve 19 for covering the needle carrier is engaged on the bushing 1701 mounted with the needle carrier 18, the head of the needle can project out of the needle hole. In the meantime, the closed front end of the sleeve 19 for covering said needle carrier presses against the leading end of the spring 20 and pre-compresses the spring 20 between the above-mentioned closed front end and the flaring base of the needle carrier 18.

The plunger can be the barrel-like plunger for use with the needle-retractable safety syringe according to the embodiment 9.

The barrel-like plunger is mounted in the syringe barrel 17. When the barrel-like plunger is pushed to the end of a cavity of the syringe barrel 17, the pushing post 2 or the tubular front end portion of the barrel 1 urges the O-ring 21 to move entirely or partly so that the fixation of the needle carrier 18 and the bushing 1701 can be relieved and at the same time, the rear end of the syringe barrel 17 relieves the engagement between the supporting member 3 and the barrel 1 present in the barrel-like plunger.

Embodiment 13

Figure 22:
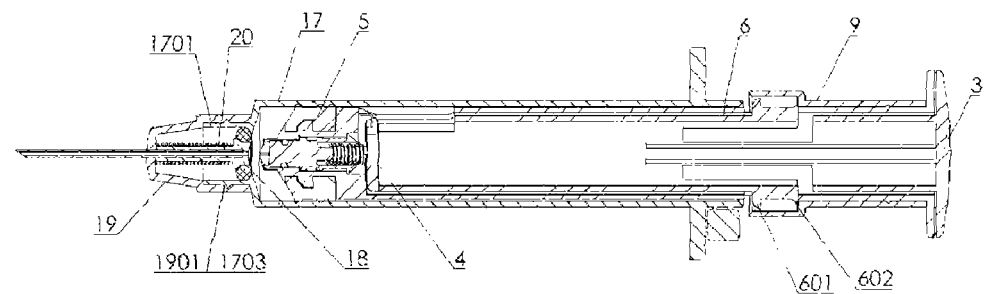
FIG. 22 is a cross sectional view of the needle-retracted controlled safety syringe according to the embodiment 13 of the present invention.

As shown in FIG. 22, the present embodiment provides a needle-retracted controlled safety syringe, the structure of which is substantially the same as that of the needle-retracted controlled safety syringe as described in the embodiment 12. The differences between the needle-retracted controlled safety syringes of embodiments 12 and 13 lie in the following features:

The plunger can be the barrel-like plunger for use with the needle-retractable safety syringe according to the embodiment 10.

The needle hole at the front end of the sleeve 19 for covering said needle carrier has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Embodiment 14

Figure 23:
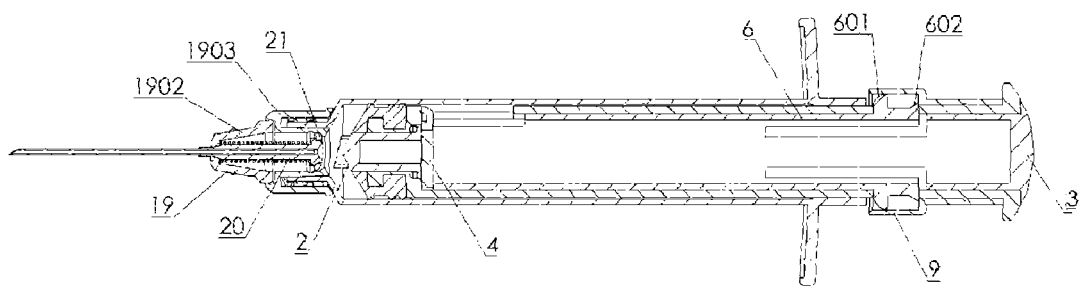
FIG. 23 is a cross sectional view of the needle-retracted controlled safety syringe according to the embodiment 14 of the present invention.
Figure 26:
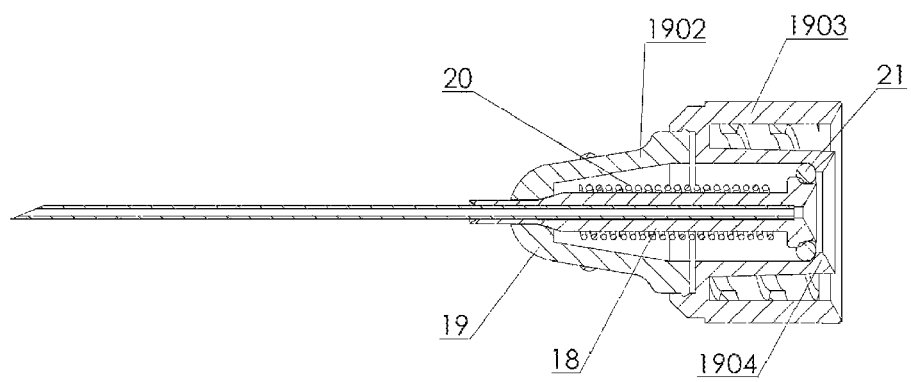
FIG. 26 is an enlarged cross sectional view of the needle head mounted on the needle-retracted controlled safety syringe according to the embodiments 14 and 15 of the present invention.

As shown in FIGS. 23 and 26, the present embodiment provides a needle-retracted controlled safety syringe which comprises a syringe barrel 17, a needle carrier 18 carrying a needle, a sleeve 19 for covering the needle carrier 18, a spring 20, an O-ring 21 and a plunger.

A shoulder is formed at the front end of the syringe barrel 17 and is shrunk toward the axial direction of the syringe barrel 17. A bushing 1701 extends forwardly from the shoulder. The diameter of the bushing 1701 is set to be smaller than the diameter of the syringe barrel 17.

The needle carrier 18 is of a tubular body having a through hole provided at its middle centre. A needle is secured in the through hole of the needle carrier 18. A flaring base is provided at the rear end of the needle carrier 18.

The sleeve 19 for covering the needle carrier 18 includes a first sleeve 1902 which has a closed front end and is provided with a needle hole and a second sleeve 1903. The inner wall of the rear end portion of the second sleeve 1903 is provided with a flange 1904. The first sleeve 1902 and the second sleeve 1903 can be connected as an entirety by means of screw connection, plugging and snapping-in.

The O-ring 21 is arranged on a narrower portion of the flaring base of the needle carrier 18 and is fitted with the flange 1904 provided at the inner wall of the rear end portion of the second sleeve 1903. In this way, the needle carrier 18 can be detachably mounted in the sleeve 19 for covering the needle carrier 18.

The spring 20 is fitted over the needle carrier 18. Also, its rear end is supported on the flaring base of the needle carrier 18.

The needle carrier 18 is mounted in the sleeve 19 for covering said needle carrier. The head of the needle can project out of the needle hole formed at the front end of the first sleeve 1902. The closed front end of the first sleeve 1902 presses against the leading end of the spring 20 and pre-compresses the spring 20 between the closed front end and the flaring base of the needle carrier 18.

The sleeve 19 for covering the needle carrier can be detachably connected to the bushing 1701 of the syringe barrel 17 by means of snapping-on, plugging or screw connection.

The plunger can be the barrel-like plunger for use with the needle-retractable safety syringe according to the embodiment 1.

The barrel-like plunger is mounted in the syringe barrel 17. When the barrel-like plunger is pushed to the end of a cavity of the syringe barrel 17, a front end of the plunger urges the O-ring 21 to move entirely or partly. As a result, the fixation of the needle carrier 18 and the sleeve 19 for covering the needle carrier can be relieved and at the same time, the rear end of the syringe barrel 17 can relieve the engagement between the supporting member 3 and the barrel 1 present in the barrel-like plunger so that the supporting member 3 is released. The needle hole at the front end of the first sleeve 1902 has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Embodiment 15

Figure 24:
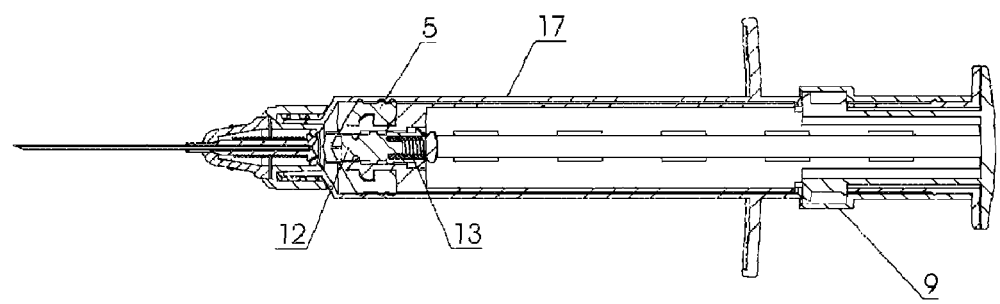
FIG. 24 is a cross sectional view of the needle-retracted controlled safety syringe according to the embodiment 15 of the present invention.
Figure 25:
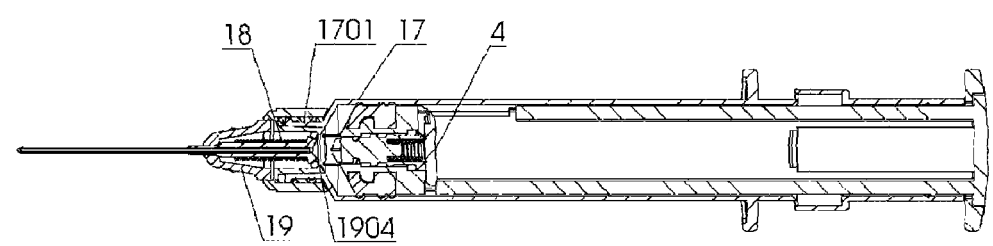
FIG. 25 is a cross sectional view of the needle-retracted controlled safety syringe shown in FIG. 24 taken along the centre line of the same.

As shown in FIGS. 24, 25 and 26, the present embodiment provides a needle-retracted controlled safety syringe, the structure of which is substantially the same as that of the needle-retracted controlled safety syringe as described in the embodiment 14. The differences between the needle-retracted controlled safety syringes of embodiments 14 and 15 lie in the following features:

The plunger can be the barrel-like plunger for use with the needle-retractable safety syringe according to the embodiment 8.

The needle hole at the front end of the first sleeve 1902 has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Embodiment 16

The present embodiment provides a needle-retracted controlled safety syringe, the structure of which is substantially the same as that of the needle-retracted controlled safety syringe as described in the embodiment 14. The differences between the needle-retracted controlled safety syringes of embodiments 14 and 16 lie in the following features:

The plunger can be the barrel-like plunger for use with the needle-retractable safety syringe according to the embodiment 11.

The needle hole at the front end of the sleeve 19 for covering the needle carrier has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Figure 27:
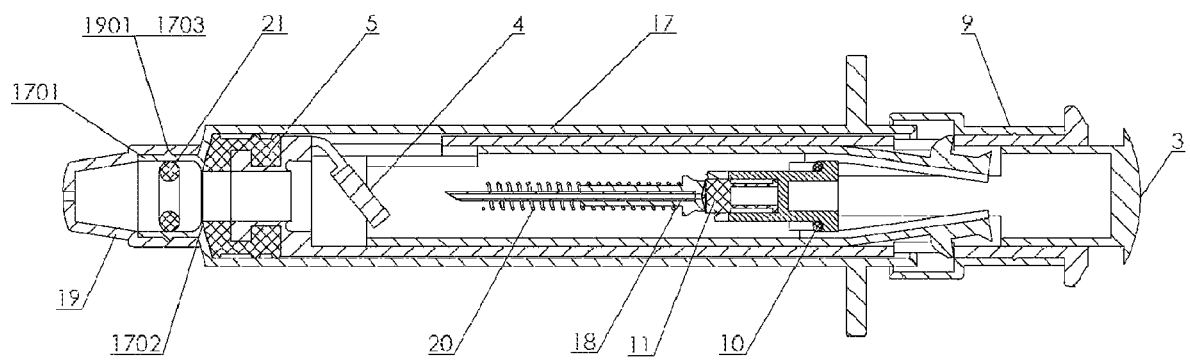
FIG. 27 is a cross sectional view showing the barrel type plunger according to the embodiment 9 of the present invention and the needle-retracted controlled safety syringe according to the embodiment 12 of the present invention under the condition where the needle has been retracted.

Next, the fundamental work principle of the invention will be explained with reference to FIG. 21 and FIG. 27 as an example.

FIG. 21 is a cross sectional view showing the barrel type plunger according to the embodiment 9 of the present invention and the needle-retracted controlled safety syringe according to the embodiment 12 of the present invention. When a user pushes the base 301 of the supporting member 3 in order to push the barrel-like plunger to the end of a cavity at the front end of the syringe barrel 17, the pushing post 2 or the tubular front end portion of the barrel 1 urges the O-ring 21 to move entirely or partly so that the fixation of the needle carrier 18 and the bushing 1701 can be relieved. In the meantime, the flexible rib 6 is deflected towards the interior of the barrel because the first projection 601 receives a backward pressing force from the rear end of the syringe barrel. As a result, the engagement between the supporting member 3 and the barrel 1 is relieved. When the user removes the force acted on the base 301, the backward force exerted by the precompressed spring 20 makes the supporting member 3 to move backwards so as to return the bearing piece 4 to its home position, while the needle can be retracted back to the interior of the barrel, as shown in FIG. 27.

While this invention has been described in conjunction with the exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments of the invention, as set forth above, are intended to be illustrative, not limiting. Various changes may be made without departing from the spirit and scope of the invention. Therefore, the invention is intended to embrace all known or later developed alternatives, modifications, variations, improvements and/or substantial equivalents.

The invention claimed is:

1. An improved barrel type plunger for use with a needle-retractable safety syringe, the plunger comprising:
   a barrel comprising a front portion which is fitted over a sealing rubber pad;
   a needle retracted trigger; and
   a supporting member;
   wherein:
      a slotted hole is disposed at a wall of the front portion of said barrel;
      a bearing piece is disposed in said slotted hole;
      one end of said bearing piece is connected to a front side wall of said slotted hole;
      said bearing piece is deflected laterally towards an interior of said barrel such that said bearing piece is resettable in order to support said needle retracted trigger;
      said needle retracted trigger is disposed at a front end of a cavity of said barrel and is supported on said bearing piece which has been deflected laterally;
      said supporting member is disposed in said barrel, a front end of said supporting member supporting said bearing piece which has been deflected laterally, and a rear end of said supporting member comprises a base for sealing the opening at a rear end of said barrel;
      said barrel and said supporting member each comprising a snap-in structure respectively, which are releasably engaged cooperatively with one another; and
      said supporting member translates backwards under the action of a needle retraction force so that said bearing piece is returned to a position wherein said needle retracted trigger and said needle are retracted backwards to the interior of said barrel.

2. The barrel type plunger for use with a needle-retractable safety syringe according to claim 1, wherein said needle retracted trigger comprises a pushing post having a closed front portion; the front end of said pushing post being projected beyond an opening of a barrel cavity formed at the front end of said barrel and said sealing rubber pad and the projected portion comprises one of a tubular structure with a flush end and a tubular structure having an end with longitudinally extending gear-like projections.

3. The barrel type plunger for use with a needle-retractable safety syringe according to claim 2, wherein:
   said supporting member comprises:
   a barrel body having an opened front end portion and a closed rear end, a wall of a rear portion of said barrel body comprising at least one opening;
   a flexible rib extending forwardly along an axial direction of said barrel body from a rear inner wall of each at least one said opening; and
   an outer wall of said flexible rib comprising a first projection which is in a shape of one of a semi-sphere, triangle or other shape comprising a slanted top end surface; and
   a wall of said barrel comprises a window at a position corresponding to a position of said first projection; and said first projection is supported at a rear edge of said window and is projecting beyond said window so that said supporting member can be releasably engaged in said barrel.

4. The barrel type plunger for use with a needle-retractable safety syringe according to claim 3, wherein:
   a notch which restores said bearing piece is formed on the wall of the front end portion of said supporting member at a position corresponding to a home position of said bearing piece; and
   said at least one opening and said window comprise a plurality of openings and a plurality of windows, respectively, and are disposed opposite to each other, respectively, each of said at least one openings having a flexible rib therein, and one first projection is provided on an outer wall of each of said flexible ribs at the same level.

5. The barrel type plunger for use with a needle-retractable safety syringe according to claim 2, wherein:
   said slotted hole, which is provided on a wall of the front portion of said barrel, extends toward a middle-rear part of said barrel, and a slotted hole is formed on a wall of said barrel opposed to said slotted hole;
   said supporting member includes the base, two flexible ribs and two first projections, said two flexible ribs being disposed oppositely on a front end surface of said base and extending forwardly along the axial direction of said barrel, said flexible ribs engaging with said two slotted holes, respectively, said two first projections being disposed on outer walls of said two flexible ribs, respectively, and comprise a shape of one of a semi-sphere, triangle and other shape comprising a slanted top end surface;
   said two first projections being supported at a rear edge of said two slotted holes, respectively, and projecting beyond said slotted holes so that said supporting member releasably engages in said barrel; and
   said bearing piece being supported by a front end of at least one of said flexible rib upon being deflected laterally.

6. The barrel type plunger for use with a needle-retractable safety syringe according to claim 2, wherein:
   a wall of the middle-rear part of said barrel comprises two opposed windows;
   said supporting member includes the base, two flexible ribs and a supporting bar, said flexible ribs and the supporting bar each being disposed on a front end surface of said base and extending forwardly along the axial direction of said barrel, outer walls of said two flexible ribs comprise a first projection, respectively, which comprises one of a shape of a semi-sphere, a triangle or other shape comprising a slanted top end surface, a length of said supporting bar disposed at a position where said bearing piece is disposed in the cavity of said barrel after the bearing piece has been deflected laterally, an arrangement orientation of said supporting bar on said base matches to an arrangement orientation of said bearing piece so that said bearing piece is supported by a front end of said supporting bar after said bearing piece has been deflected laterally; and
   said first projection is supported at a rear edge of said window and projects beyond said window so that said supporting member releasably engages in said barrel.

7. The barrel type plunger for use with a needle-retractable safety syringe according to any one of claim 3-6, wherein a projected retaining ring is disposed in a circle along an inner wall of the rear portion of said barrel so that said supporting member will be blocked by said retaining ring again after it has been moved backwards to such an extent that said bearing piece returns to a home position.

8. The barrel type plunger for use with a needle-retractable safety syringe according to claim 3, 4 or 6, wherein:
   the outer wall of said flexible rib further comprises a second projection thereon, which is disposed behind said first projection, a distance between a rear end surface of said first projection and a rear end surface of said respective second projection is set to be equal to or larger than a backward movement distance of said supporting member required for returning said bearing piece to a position where said pushing post and the needle can be retracted back to the interior of said barrel, and a projecting height of said respective second projection is set to be smaller than or equal to a projecting height of said first projection; and
   said first projection and said second projection are mounted in said window and extend beyond said window, said second projection is supported by the rear edge of said window so that said supporting member releasably engages said barrel.

9. The barrel type plunger for use with a needle-retractable safety syringe according to claim 2, wherein:
   at least one window is formed on a wall of a middle-rear part of said barrel;
   said supporting member comprises:
      a barrel body comprising an opened front end and a closed rear end;
      at least one opening disposed on a wall of a middle-rear portion of said barrel body at a position corresponding to the position of each window;
      at least one flexible rib extending backwards along an axial direction of said barrel body formed on a front side wall of said opening, an outer wall of each said at least one flexible rib comprising a first projection thereon, the first projection comprising a shape of one of a semi-sphere, a triangle or other shape having a slanted top end surface; and
   said first projection being supported at a rear edge of said window and projecting beyond said window so that said supporting member releasably engages in said barrel.

10. The barrel type plunger for use with a needle-retractable safety syringe according to claim 9, wherein:
   a notch which restores said bearing piece is provided on a wall of a front end portion of said supporting member at a position corresponding to a home position of said bearing piece;
   each of the at least one windows is disposed on the wall of said barrel and the at least one opening is disposed on the wall of said supporting member are a plurality of windows and a plurality of openings, and are substantially symmetrical, respectively, and at least one said flexible ribs and said first projections provided thereon are a plurality of flexible ribs and a plurality of first projections and are substantially symmetrical, respectively;
   said at least one flexible rib further comprises a second projection thereon, which is disposed behind said first projection, a distance between a rear end surface of said first projection and a rear end surface of said second projection is equal to or larger than a backward movement distance of said supporting member required for returning said bearing piece to a position where said pushing post and the needle can be retracted back to the interior of said barrel, and a projecting height of said second projection is smaller than or equal to a projecting height of said first projection; and said first projection and said second projection are each mounted in said window and extend beyond said window, said second projection being supported by a rear edge of said window so that said supporting member releasably engages in said barrel.

11. The barrel type plunger for use with a needle-retractable safety syringe according to claim 3, wherein:
said supporting member comprises a front barrel and a rear barrel which are nested one on the top of another;
a notch which restores said bearing piece is disposed on a wall of a front end portion of said front barrel at a position which corresponds to a home position of said bearing piece, a rear end of said front barrel and a front end of said rear barrel are provided with a socket and spigot joint, respectively, which engages to each other;
said opening is disposed on a wall of said rear barrel behind the portion which is jointed to said front barrel.

12. The barrel type plunger for use with a needle-retractable safety syringe according to claim 11, wherein:
an outer diameter of a portion at the front end of said rear barrel which is joined to said front barrel is smaller than an outer diameter of other portions of said rear barrel and matches an inner diameter of said front barrel, a set piece is disposed on a portion at the front end of said rear barrel which is joined to said front barrel;
one of a locating slot and a locating hole which fits to said set piece is disposed on a wall of the rear end portion of said front barrel at a portion which is joined to said rear barrel;
a second projection is disposed behind said first projection, a projecting height of said first projection is larger than or equal to a projecting height of said second projection, and a distance between a rear end surface of said first projection and a rear end surface of said second projection is equal to or larger than a backward movement distance of said supporting member required for returning said bearing piece to a position where said pushing post and the needle can be retracted back to the interior of said barrel; and
said first projection and said second projection are each mounted in the window and extend beyond said window, said second projection is supported by the rear edge of said window so that said supporting member releasably engages in said barrel.

13. The barrel type plunger for use with a needle-retractable safety syringe according to any one of claims 2-6 and 9-12, further comprising:
a protective sleeve, comprising a thicker tubing and a thinner tubing which are connected together; an inner diameter of said thicker tubing being larger than or equal to the outer diameter of a syringe barrel of the syringe;
a flange disposed in a circle on an outer wall of a rear portion of said barrel;
an inner diameter of said thinner tubing which matches an outer diameter of said barrel; and
a recess which engages with said flange being disposed in a circle on an inner wall of said thinner tubing;
wherein said protective sleeve is fitted to the rear end of said barrel and is secured thereon by means of the engagement of said recess and said flange so that the thicker tubing surrounds the engaged portion where said barrel and said supporting member are engaged to each other.

14. The barrel type plunger for use with a needle-retractable safety syringe according to claim 13, further comprising:
a sealing pad and a compressible needle stop member, said sealing pad being mounted between the walls of said pushing post and the front end of said barrel; and
the front portion of said pushing post comprises a chamber, in which said needle stop member is disposed, a leading end of said needle stop member projecting beyond the front end of said pushing post after it has blocked the opening of the chamber of said pushing post.

15. The barrel type plunger for use with a needle-retractable safety syringe according to claim 13, wherein:
a tubular front end portion comprising one of a flush end and an end having longitudinally extending gear-like protrusions is exposed after said barrel is fitted with said sealing rubber pad;
said pushing post can be replaced with a compressible needle stop member comprising a stop post and a spring which is fitted over a rear portion of said stop post and supports said stop post;
a cavity disposed at the front end of said barrel which arranges said needle stop member comprises a front chamber and a rear chamber, an inner diameter of said front chamber matches an outer diameter of said stop post, and an inner diameter of said rear chamber is larger than the outer diameter of said stop post;
a recess is disposed in a circle on a portion of said stop post corresponding to said front chamber, a sealing ring is disposed in said recess, a projected orientation ring is disposed in at least one circle on such a portion of said stop post that corresponds to a position of said rear chamber, an outer diameter of said orientation ring matches the inner diameter of said rear chamber;
a leading end of said needle stop member projects out of the front end of said barrel after it has blocked opening at the front end of said barrel, and a rear end of said needle stop member is compressed and is supported on said bearing piece;
a front end surface of said stop post comprises a recess; and
a wall of the tubular front end portion of said barrel comprises a slot which communicates with said recess.

16. A needle-retracted controlled safety syringe, comprising a syringe barrel, a needle carrier which carries a needle, a sleeve which covers said needle carrier, a spring, an O-ring and a plunger,
wherein:
said plunger comprises a barrel-like plunger according to claim 13;
a shoulder is disposed at a front end of said syringe barrel and is shrunk toward an axial direction of said syringe barrel;
a bushing extends forwardly from said shoulder;
a flange is disposed on a portion of an inner wall of said bushing which is connected to said shoulder; and
one of a snap-on, plug-connected and screw connection structure is disposed on the outer wall of said bushing;
said needle carrier comprises: a tubular body having a through hole disposed at its center and secures a needle therein, and a flaring base disposed at a rear end of said needle carrier, said needle carrier being installed in said bushing;
said O-ring is arranged on a narrower portion of said flaring base of said needle carrier and is fitted with said flange provided at the inner wall of said bushing so that said needle carrier is detachably mounted in said bushing;
said spring is fitted over said needle carrier, and a rear end of said spring is supported on said flaring base of said needle carrier;

said sleeve which covers said needle carrier has a cavity opened backwards, the inner diameter of said cavity matching the outer diameter of said bushing, and an inner wall of said sleeve which covers said needle carrier comprises one of a snap-on, plug-connected and screw connection structure which engages with said one of snap-on, plug-connected or screw connection structure disposed on the outer wall of said bushing;

a closed front end of said sleeve which covers said needle carrier comprises a needle hole; and when said sleeve which covers said needle carrier is attached to said bushing mounted with said needle carrier, a head of said needle can project out of said needle hole, the closed front end of said sleeve which covers said needle carrier presses against the leading end of said spring and pre-compresses said spring between said closed front end and said flaring base of said needle carrier;

said barrel-like plunger is mounted in said syringe barrel, and when said barrel-like plunger is pushed to an end of a cavity of said syringe barrel, one of a pushing post and a tubular front end portion of a barrel of said barrel-like plunger urges said O-ring to move so that the fixation of said needle carrier and said bushing is relieved, while a rear end of said syringe barrel relieves the engagement between a supporting member and said barrel present in said barrel-like plunger and releases said supporting member.

17. An improved barrel type plunger for use with a needle-retractable safety syringe, the plunger comprising:
   a barrel comprising a front portion which is fitted over a sealing rubber pad;
   a needle carrying member;
   a tubular front end portion with one of a flush end and an end having longitudinally extending gear-like protrusions being exposed after said barrel is fitted with said sealing rubber pad; and
   a supporting member;
   wherein:
   a slotted hole is disposed at a wall of a front portion of said barrel;
   a bearing piece is disposed in said slotted hole;
   one end of said bearing piece is connected to a front side wall of said slotted hole;
   said bearing piece is deflected laterally towards an interior of said barrel such that said bearing piece is resettable in order to support said needle carrying member;
   said needle carrying member is disposed at a front end of a cavity of said barrel and is supported on said bearing piece which has been deflected laterally;
   said supporting member is disposed in said barrel, a front end of said supporting member supporting said bearing piece which has been deflected laterally, and a rear end of said supporting member comprises a base for sealing the opening at a rear end of said barrel;
   said barrel and said supporting member each comprising a snap-in structure respectively, which are releasably engaged cooperatively with one another; and
   said supporting member translates backwards under the action of a needle retraction force so that said bearing piece is returned to a position wherein said needle carrying member and said needle are retracted backwards to the interior of said barrel.

18. A needle-retracted controlled safety syringe, comprising a syringe barrel, a needle carrier which carries a needle, a sleeve which covers said needle carrier, a spring, an O-ring and a plunger, wherein:
   said plunger comprises a barrel-like plunger according to claim 13;
   a shoulder is disposed at a front end of said syringe barrel and is shrunk toward an axial direction of said syringe barrel;
   a bushing extends forwardly from said shoulder;
   said needle carrier comprises a tubular body having a through hole provided at its center and securing a needle therein, and a flaring base disposed at a rear end of said needle carrier;
   said sleeve which covers said needle carrier comprises a first sleeve which comprises a closed front end, a needle hole and a second sleeve, an inner wall of a rear end portion of the second sleeve is comprises a flange;
   said first sleeve and said second sleeve are connected as an entirety by one of a screw connection, plugging or snapping-in and adhering or ultrasonic welding;
   said O-ring is disposed on a narrower portion of said flaring base of said needle carrier and is fitted with said flange disposed at an inner wall of said rear end portion of said second sleeve so that said needle carrier can be detachably mounted in said sleeve which covers said needle carrier;
   said spring is fitted over said needle carrier, and a rear end of said spring is supported on said flaring base of said needle carrier;
   said needle carrier is mounted in said sleeve which covers said needle carrier;
   a head of said needle can project out of said needle hole disposed at a front end of said first sleeve, a closed front end of said first sleeve presses against a leading end of said spring and pre-compresses said spring between said closed front end and said flaring base of said needle carrier;
   said sleeve which covers said needle carrier is detachably connected to said bushing of said syringe barrel by one of a snapping-on, a plugging and a screw connection;
   said barrel-like plunger is mounted in said syringe barrel, and when said barrel-like plunger is pushed to an end of a cavity of said syringe barrel, one of a pushing post and a tubular front end portion of a barrel of said barrel-like plunger pushes said O-ring to move so that a fixation of said needle carrier and said sleeve which covers said needle carrier is relieved, while a rear end of said syringe barrel relieves the engagement between a supporting member and said barrel present in said barrel-like plunger and releases said supporting member.

19. The needle-retracted controllable safety syringe according to claim 18, wherein:
   said plunger comprises a barrel-like plunger;
   the needle hole at the front end of said first sleeve comprises an inward flared structure;
   a front portion of said needle carrier comprises a cone-shaped structure, which matches to the inward flared structure; and
   said needle carrier is fixed by the flared structure of said needle hole and said cone-shaped structure disposed at the front portion of said needle carrier.

20. The needle-retracted controlled safety syringe, wherein:
   said plunger comprises a barrel-like plunger according to claim 14; the needle hole at the front end of said first sleeve comprises an inward flared structure;
   a front portion of said needle carrier comprises a cone-shaped structure, which matches to the inward flared structure; and after the assembly, said needle carrier (18) is fixed by the cooperation between the flared structure of said needle hole and said cone-shaped structure disposed at the front portion of said needle carrier.

21. The needle-retracted controlled safety syringe according to claim 16, wherein:

said plunger comprises a barrel-like plunger;

the needle hole at the front of said sleeve for covering said needle carrier comprises an inward flared structure;

the front portion of said needle carrier comprises a cone-shaped structure, which matches the inward flared structure; and said needle carrier is fixed by the flared structure of said needle hole and said cone-shaped structure disposed at the front portion of said needle carrier.

22. A needle-retracted controlled safety syringe, comprising a barrel-like plunger according to claim 17.

* * * * *

UNITED STATES PATENT AND TRADEMARK OFFICE
CERTIFICATE OF CORRECTION

| | | |
|---|---|---|
| PATENT NO. | : 7,789,855 B2 | |
| APPLICATION NO. | : 12/057656 | |
| DATED | : September 7, 2010 | |
| INVENTOR(S) | : Wenjie Liu | |

It is certified that error appears in the above-identified patent and that said Letters Patent is hereby corrected as shown below:

Column 24, line 51:

Please delete "said plunger comprises a barrel-like plunger;" and insert the following paragraphs
-- the plunger further comprises:
a tubular front end portion comprising one of a flush end and an end having longitudinally extending gear-like protrusions is exposed after said barrel is fitted with said sealing rubber pad;
said pushing post can be replaced with a compressible needle stop member comprising a stop post and a spring which is fitted over a rear portion of said stop post and supports said stop post;
a cavity disposed at the front end of said barrel which arranges said needle stop member comprises a front chamber and a rear chamber, an inner diameter of said front chamber matches an outer diameter of said stop post, and an inner diameter of said rear chamber is larger than an the outer diameter of said stop post;
a recess is disposed in a circle on a portion of said stop post corresponding to said front chamber, a sealing ring is disposed in said recess, a projected orientation ring is disposed in at least one circle on such a portion of said stop post that corresponds to a position of said rear chamber, an outer diameter of said orientation ring matches the inner diameter of said rear chamber;
a leading end of said needle stop member projects out of a the front end of said barrel after it has blocked opening at the front end of said barrel, and a rear end of said needle stop member is compressed and is supported on said bearing piece;
a front end surface of said stop post comprises a recess; and
a wall of the tubular front end portion of said barrel comprises a slot which communicates with said recess; -- and a paragraph break Signed and Sealed this
Twenty-sixth Day of July, 2011

David J. Kappos
*Director of the United States Patent and Trademark Office*

CERTIFICATE OF CORRECTION (continued)
U.S. Pat. No. 7,789,855 B2

Column 24, line 60:

After the word "syringe" please insert -- according to claim 18 --

Column 24, line 62-63:

Please delete "said plunger comprises a barrel-like plunger according to claim 14" and insert the following paragraphs
-- the plunger further comprises:
   a sealing pad and a compressible needle stop member, said sealing pad being mounted between the walls of said pushing post and the front end of said barrel; and
   the front portion of said pushing post comprises a chamber, in which said needle stop member is disposed, a leading end of said needle stop member projecting beyond the front end of said pushing post after it has blocked the opening of the chamber of said pushing post; -- and a paragraph break

Column 25, line 7:

Please delete "said plunger comprises a barrel-like plunger;" and insert the following paragraphs
-- the plunger further comprises: a tubular front end portion comprising one of a flush end and an end having longitudinally extending gear-like protrusions is exposed after said barrel is fitted with said sealing rubber pad;
   said pushing post can be replaced with a compressible needle stop member comprising a stop post and a spring which is fitted over a rear portion of said stop post and supports said stop post;
   a cavity disposed at the front end of said barrel which arranges said needle stop member comprises a front chamber and a rear chamber, an inner diameter of said front chamber matches an outer diameter of said stop post, and an inner diameter of said rear chamber is larger than an the outer diameter of said stop post;
   a recess is disposed in a circle on a portion of said stop post corresponding to said front chamber, a sealing ring is disposed in said recess, a projected orientation ring is disposed in at least one circle on such a portion of said stop post that corresponds to a position of said rear chamber, an outer diameter of said orientation ring matches the inner diameter of said rear chamber;
   a leading end of said needle stop member projects out of a the front end of said barrel after it has blocked opening at the front end of said barrel, and a rear end of said needle stop member is compressed and is supported on said bearing piece;
   a front end surface of said stop post comprises a recess; and
   a wall of the tubular front end portion of said barrel comprises a slot which communicates with said recess; -- and a paragraph break